United States Patent [19]

McLaughlin

[11] Patent Number: 4,844,293
[45] Date of Patent: Jul. 4, 1989

[54] DISPOSABLE GLOVE DISPENSING APPARATUS

[76] Inventor: David T. McLaughlin, 279 Highgate Ave., Worthington, Ohio 43085

[21] Appl. No.: 214,060

[22] Filed: Jun. 30, 1988

[51] Int. Cl.$^4$ .............................................. B65H 1/00
[52] U.S. Cl. ...................................... 221/34; 221/59; 221/62; 221/197; 221/287; 206/278; 206/438
[58] Field of Search .................. 221/34, 45, 46, 56–61, 221/197, 312 R, 312 C, 303, 305, 307, 309; 206/278, 299, 438

[56] References Cited

U.S. PATENT DOCUMENTS

| | | | |
|---|---|---|---|
| 1,783,414 | 12/1930 | Daniels | 221/58 |
| 2,541,933 | 2/1951 | Nail | 221/61 |
| 3,870,150 | 3/1975 | Hummel | 206/438 |
| 3,942,682 | 3/1976 | McKay | 221/58 |
| 4,069,913 | 1/1978 | Harrigan | 206/438 |
| 4,773,532 | 9/1988 | Stephenson | 206/438 |

*Primary Examiner*—Joseph J. Rolla
*Assistant Examiner*—Steven Reiss
*Attorney, Agent, or Firm*—Francis T. Kremblas, Jr.

[57] ABSTRACT

A dispensing apparatus for disposable, thin plastic gloves is disclosed wherein said gloves may be retrieved by the user one at a time in a relatively simple manner. The apparatus comprises a box-like, generally rectangular enclosure for housing a removably mounted packet containing a plurality of the disposable gloves arranged in the packet in closely spaced, planar unfolded condition. The enclosure is provided with a front window or opening and a removable top cover or cap. The packet of gloves is loaded into the enclosure through a top opening and are disposed so that they may be removed, one at a time, through the front opening of the enclosure. The packet comprises a pair of faces yieldably connected to one another which have a configuration generally conforming to the shape of the gloves in an open palm and finger planar condition. The enclosure includes means to support the packet carrying the gloves in a parallel relationship with the gloves being biasly urged toward the front window to conveniently present the outermost glove to the user.

5 Claims, 1 Drawing Sheet

U.S. Patent
Jul. 4, 1989
4,844,293
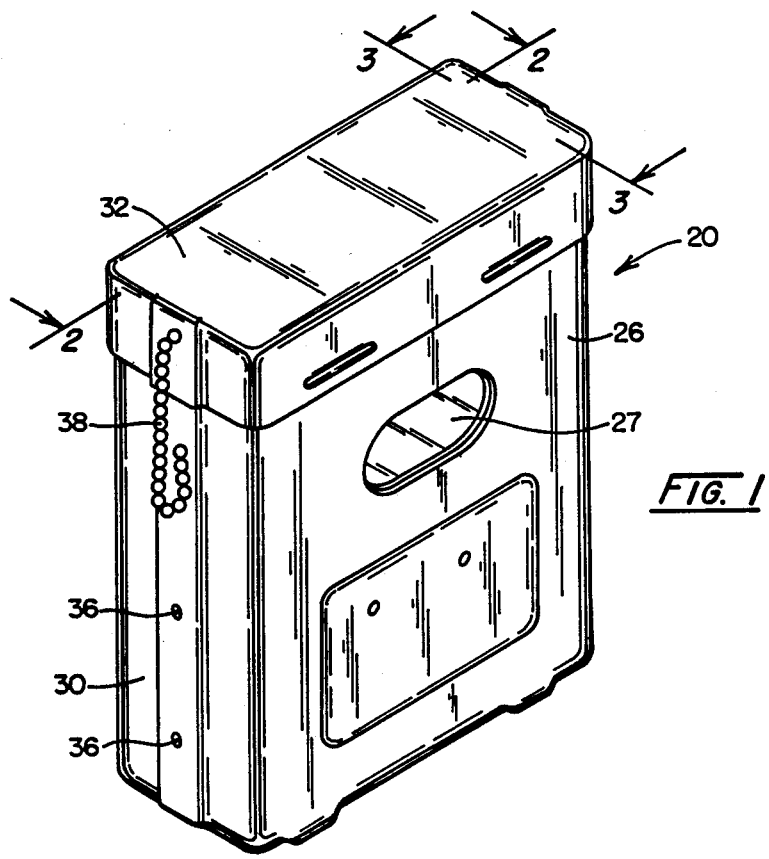
FIG. 1
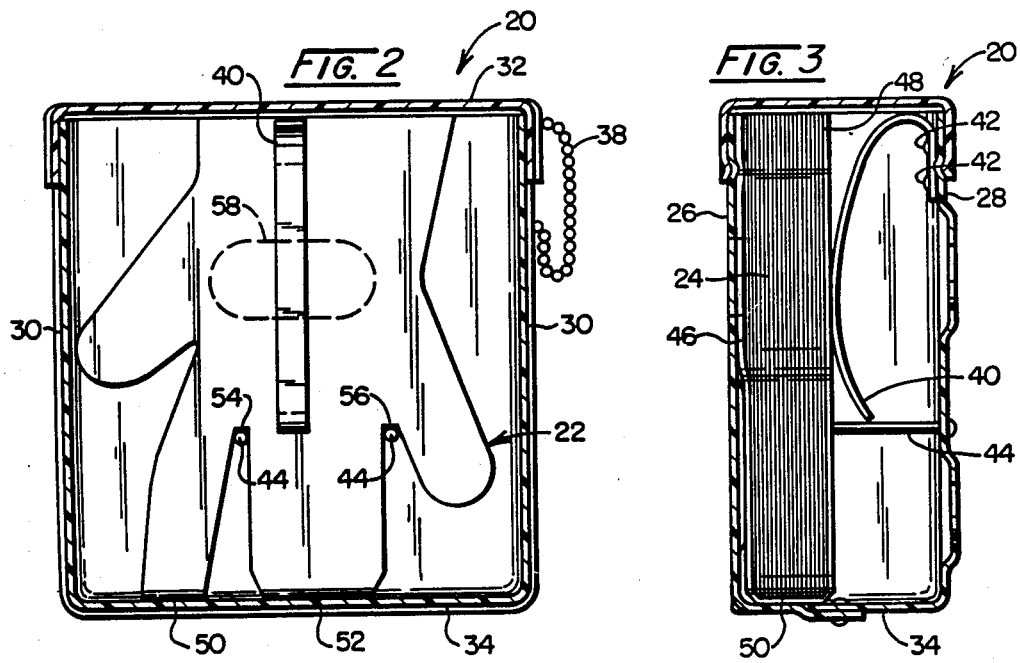
FIG. 2
FIG. 3

100
DISPOSABLE GLOVE DISPENSING APPARATUS

BACKGROUND OF THE INVENTION

Relatively thin, disposable polyethylene gloves have a variety of uses and applications in the present marketplace and have been available for many years. However, one of the major drawbacks to expanding the use or availability of such gloves resides in the manner in which they have been packaged for use or distribution to the ultimate user. Given the intended disposable nature of the gloves and the necessity of maintaining a low cost per glove, the prior means for packaging a plurality of gloves in a unit for dispensing consisted of a paperboard box containing a plurality of gloves stacked therein in a folded relationship. The other packaging means for such gloves comprised a roll of tissue paper carrying a single glove mounted on the paper roll in spaced relationship from one another along the length of the roll.

The first described means has been found less than satisfactory because it is very difficult to consistently retrieve only one glove at a time and results in an objectionable percentage of waste. Therefore too often a user pulls a plurality of gloves out of the box resulting in discarding all but the one required. The second means is not satisfactory because it is too costly for many applications or potential applications wherein such gloves otherwise might be made available for use.

Further, both of such methods for packaging such disposable gloves for easy dispensing are deficient in providing protection against the elements of weather or against waste due to casual tampering or destruction, thereby significantly hindering the use thereof in outdoor applications.

Therefore, the expansion of the use of such disposable gloves which may be desirable has been hampered by the lack of a convenient and reliable dispensing package which provides efficient one at a time retrieval of the gloves in a low cost manner and further provides a more secure and protected package vehicle which is not so cost prohibitive as to make the use of the gloves economically impractical for most applications.

SUMMARY OF INVENTION

The present invention relates to disposable glove dispensers in general and particularly to a novel, improved glove dispenser which promotes efficient dispensing of one glove at a time in a relatively low cost manner. As one aspect of the present invention, the disposable gloves are packaged in the form of a packet containing a given number of gloves. The packet is removably mounted in a relatively secure enclosure from which the gloves may be retrieved one at a time in a very convenient manner.

The novel packet includes front and rear faces which are configured generally similar to the configuration of the gloves which themselves are stacked between the faces in a full palm and fingers open, flat disposition. The packet includes a top opening and front and rear faces which are connected or closed at the bottom along the ends thereof commensurate with the middle three fingers of the gloves. The packet also includes a closure supporting the webbing at the base between the ring finger and the little finger and between the middle and index finger which define a stop means limiting the depth the gloves are positioned between the faces of the packet.

As a further aspect of the present invention, the enclosure includes a pair of spaced pins located therein to provide support for the removable packet which in cooperation with the faces of the packet and a leaf spring mounted in the enclosure, dispose the gloves in a suitable position to be retrieved through aligned openings in one face of the packet and in a front wall of the enclosure.

It is therefore an object of the present invention to provide an efficient disposable glove dispenser which includes a packet containing a plurality of disposable gloves removably mounted in a secure enclosure in a manner which promotes easy removal of one glove at a time.

It is another object of the present invention to provide a novel packet or package of a plurality of disposable gloves wherein the packet is mounted within the protecting enclosure in a collapsible manner to assure that the top glove of the stack of gloves is always biased against the openings through which the gloves are to be removed. This feature provides essentially the same level of ease of removal irrespective of the number of gloves remaining in the packet until the last glove in the packet is removed.

It is still another object of the present invention to provide a disposable glove dispenser of the type described wherein a permanent type of outer enclosure and a removably mounted packet of disposable gloves cooperate to position the gloves for easy retrieval and yet permit securing the outer enclosure to discourage casual tampering or theft of the whole packet of gloves stored inside the enclosure.

It is a further object of the present invention to provide a disposable glove dispenser which includes an outer enclosure providing a significant degree of protection against the elements of the weather to promote use in outdoor applications, as well as withstanding wet conditions such as encountered in food and meat processing applications.

Further objects and advantages of the present invention will be apparent from the following description, reference being had to the accompanying drawings wherein a preferred form of embodiment of the invention is clearly shown.

IN THE DRAWINGS

FIG. 1 is a perspective view of a disposable glove dispenser constructed in accordance with the present invention;

FIG. 2 is a front elevational view, in section, of the dispenser shown in FIG. 1, the section being taken along line 2—2 in FIG. 1; and FIG. 3 is a side elevational view, in section, of the dispenser shown in the preceding Figures, the section being taken along line 3—3 in FIG. 1.

DETAILED DESCRIPTION OF THE DRAWINGS

A disposable glove dispenser constructed in accordance with the present invention is shown in FIGS. 1-3 and includes an outer rigid enclosure, indicated generally at 20. A packet or package indicated generally at 22, containing a plurality of gloves 24, is removably mounted within enclosure 20.

Enclosure 20 is preferably made from a conventional plastic material which may be easily manufactured using standard molding techniques and fabricated in a relatively inexpensive manner. However, other types of suitable materials, such as metal, wood or the like which provide sufficient strength and resistance to weather elements for the intended application may be used without departing from the spirit of the present invention.

Enclosure 20 includes front and rear wall means 26, 28, side walls 30, and bottom wall 34. A cover 32 is removably mounted in the form of a cap-like member, however, it could be suitably conventionally hinged or be constructed in any other well-known manner to provide convenient protected access to the top opening of the interior of enclosure 20.

Front wall 26 is provided with a window or opening 27 to the interior of enclosure 20 for access to the gloves stored therein as described in detail later herein.

As shown in FIG. 1, enclosure 20 is formed in a box-like configuration from molded half portions which are riveted together such as at 36. Cover 32 merely slides over the front and side walls of enclosure 20. A chain 38 connected to the cover 32 and a side wall 30 merely is for convenience to keep those portions from together when the cover 32 is removed.

The interior of enclosure 20 includes a leaf spring 40 fixed to rear wall 28 by a pair of rivets 42. A pair of horizontally extending, spaced pins 44 are connected between the front and rear walls to support the packet 22 as described later herein.

Packet 22 includes a front face 46 and a rear face 48 which are connected to one another at the ends of the index finger similar to a glove and at the ends of that portion relating to the middle and ring finger of a glove such as seen at 50 and 52. The top portions of each face 46, 48 are not connected to permit easy assembly of the gloves in the packet and so not to interfere with the yieldability of the faces collapsing toward one another when pressure is applied perpendicular to the plane of the faces.

Preferably, the faces 46 and 48 consist of inexpensive cardboard type of material which provides a minimum sufficient degree of stiffness to aid in supporting the thin plastic gloves stacked therebetween. The connecting portions 50 and 52 are of the same material and preferably are provided with folds or the like so as not to interfere with the collapsible nature of the packet described above. As will become evident herein, it is important that the faces of packet 22 are constructed to be collapsed toward one another such as to reduce the distance between the faces as the number of gloves therebetween is decreased.

The faces of packet 22 are yieldably connected to one another along an edge defining the webbing between the base of the index finger and the middle finger and at the base between the ring finger and the little finger, such as at 54 and 56. These connections serve to provide a stop to locate the stack of gloves contained between the faces and aid in supporting the gloves to prevent collapse from the desired open palm and finger, planar configuration as seen in FIGS. 2 and 3. Further, the connections 54 and 56 described above also cooperate with pins 44 to support and locate the packet 22 within the enclosure to align opening 27 and a window or opening 58 provided in front face 46 for access to the stack of gloves 24 when the packet is loaded within enclosure 20 in the proper manner.

To properly use the dispenser of the present invention, the user removes cover 32 and loads a packet 22 carrying a stack of disposable gloves 24 into enclosure 20. The packet 22 and gloves 24 are inserted with the finger portions pointed downwardly, as seen in FIG. 2, between the front wall 26 and leaf spring 40 until the connections 54 and 56 rest upon pins 44. With appropriate dimensioning, the openings 27 and 58 are aligned with one another to expose the top glove in the stack of gloves 24. The cover 32 is then replaced and the dispenser is ready to use.

The enclosure 20 may be provided with any appropriate hardware of conventional design so as to permit it to be hung on a wall or the like.

For example, rear wall 48 may include suitable conventional slots or holes adapted to receive a pin-like member fixed to a wall to enable enclosure 20 to be hung from the wall. In other applications, particularly for outdoor use, more secure means may be employed to conventionally position enclosure 20 for convenient use.

Once enclosure 20 is loaded with a packet 22 as described herein, a disposable glove 24 may be easily removed through openings 27 and 58. It is relatively easy to remove the gloves one at a time because the gloves are not in a folded condition and the stack of gloves 24 are biasly urged toward the openings by the pressure of spring 40. Even as the number of gloves in packet 22 decline, the pressure of spring 40 urges the rear face and the remaining gloves 24 toward the front face 46 and the openings 27 and 58 as the faces, in effect, collapse toward one another. This tends to assure the last few remaining gloves 24 are presented to the user in a similar manner as if the packet 22 were full.

When the gloves 24 become exhausted, a new packet 22 of glove 24 may be inserted as previously described after the exhausted packet is simply removed through the top of the enclosure after cover 32 is removed.

In view of the foregoing description, it should be readily appreciated that a disposable glove dispenser is provided which promotes efficient one at a time removal of a thin, flexible plastic glove in a very easy fashion. Further, the permanent, sturdy, and re-usable enclosure 20 cooperates with packet 22 to provide the ease of dispensing a single glove and yet offers improved protection to promote outdoor use of the disposal gloves. It should be appreciated that a more secure cover or lid, such as 32, could be easily designed using conventional methods where deemed necessary to provide a means for locking the cover in place to discourage unauthorized removal of the whole packet 22 without departing from the present invention.

Additionally, it should be pointed out that the initial cost of the permanent and re-usable enclosure 20 is greatly minimized over a reasonable short period of use so as to add minimal expense on a per glove basis over the useful life of the enclosure 20.

I claim:

1. A dispensing apparatus for disposable gloves comprising, in combination,
   (a) a generally rectangular, rigid enclosure having at least two spaced, parallel extending wall means, a top opening and a window in one of said wall means, said top opening and said window providing interior access to said enclosure;
   (b) a packet having a pair of spaced parallel extending faces yieldably connected to one another and removably mounted in said enclosure through said top opening, said faces having a configuration generally similar to a full glove in an open palm and finger disposition, one of said faces having an opening aligned with the window in said wall means of said enclosure;

(c) a plurality of gloves mounted in said packet between said faces in a stacked, parallel extending relationship with one another and parallel to said faces of said packet in an open palm and finger relationship;

(d) and means mounted in said enclosure for biasing said faces of said packet and the stack of gloves toward said window in said wall means to urge an outermost glove in said stack of gloves closely adjacent to said window.

2. The apparatus defined in claim 1 including connecting means for yieldably connecting said faces of said packet to one another along an edge of said faces generally co-incident to the base between the index and middle fingers and the base between the ring and little fingers; and wherein said enclosure includes a pair of parallel pin members extending generally at a right angle between said parallel extending wall means and located to engage said connecting means of said packet when said opening in one of said faces is aligned adjacent to the window in one of said wall means.

3. The apparatus defined in claim 1 wherein said means defined in (d) comprises a leaf spring mounted in said enclosure to engage the face of said packet opposite of said face having said opening to urge said faces toward said window in said wall means.

4. A dispensing apparatus for disposable human gloves comprising, in combination, (a) a generally rectangular, rigid enclosure including a top opening, a rear wall and a front wall having a window providing interior access to said enclosure and including a pair of parallel pin members extending at a right angle between said front and rear wall in spaced relationship from one another;

(b) a packet containing a plurality of disposable gloves removably mounted through said top opening into said enclosure, said packet including a front and rear face extending parallel to and spaced from one another, each of said faces having a planar configuration generally similar to an open palm and finger portions of said gloves, said gloves being mounted between said faces in stacked overlapping, parallel relationship to one another and to said faces in a palm and fingers open, planar relationship;

(c) means yieldably connecting said faces of said packet along an edge defining a stop means for positioning said gloves between said faces, said stop means being generally co-incident with the webbing at the base between the index and middle fingers and the ring and little fingers of said gloves.

(d) an opening disposed in said front face of said packet providing access to said stack of gloves, said opening being aligned with said window in the front wall of said enclosure when said packet is mounted in said enclosure with said stop means engaging said parallel pin members in said enclosure;

(e) and spring means mounted in said enclosure and engaging the rear face of said packet for urging said faces of said packet and the gloves therebetween toward said window in the front wall of said enclosure.

5. A packet containing a plurality of disposable gloves for removably loading the packet in a predetermined relationship within a rigid outer enclosure for dispensing said gloves one at a time through an opening in said enclosure comprising, in combination, (a) a front and rear face extending parallel to and spaced from one another, each of said faces having a planar configuration generally similar to said gloves disposed in an open palm and digit disposition;

(b) a plurality of disposable gloves disposed in said packet between said faces in an open palm and digit, parallel extending, overlying relationship to one another and in parallel extending relationship to said faces;

(c) means yieldably connecting said faces of said packet to one another along at least two separate edge portions defining a stop means for limiting the position of said stack of gloves relative to said faces when said gloves are aligned generally co-incident palm and digit relationship to the configuration of said faces, said stop means being formed at the base portion between adjacent pairs of said digits formed in said faces;

(d) and an opening in one of said faces providing access to the outermost glove in said stack of gloves disposed between said faces.

* * * * *